United States Patent [19]
Davsko

[11] Patent Number: 6,078,261
[45] Date of Patent: Jun. 20, 2000

[54] SYSTEM FOR MONITORING A BED PATIENT

[75] Inventor: John L. Davsko, Tulsa, Okla.

[73] Assignee: Alert Systems, Inc., Tulsa, Okla.

[21] Appl. No.: 09/189,385

[22] Filed: Nov. 10, 1998

[51] Int. Cl.[7] .................................................. G08B 23/00
[52] U.S. Cl. .................. 340/573.4; 340/539; 340/691.4; 340/691.5; 340/692; 340/572; 340/573; 200/85 R
[58] Field of Search ................................ 340/573.4, 666, 340/539, 691.4, 691.5, 692, 529, 691.1, 571, 568, 572, 573; 200/85 R

[56] References Cited

U.S. PATENT DOCUMENTS

| | | | |
|---|---|---|---|
| 4,179,692 | 12/1979 | Vance | 340/573 |
| 4,295,133 | 10/1981 | Vance | 340/573 |
| 4,484,043 | 11/1984 | Musick et al. | 200/85 R |
| 4,565,910 | 1/1986 | Musick et al. | 200/85 R |
| 4,700,180 | 10/1987 | Vance | 340/573 |
| 4,907,845 | 3/1990 | Wood | 340/573.4 |
| 5,184,112 | 2/1993 | Gusakov | 340/573 |
| 5,235,319 | 8/1993 | Hill et al. | 340/573.4 |
| 5,353,012 | 10/1994 | Barham et al. | 340/573 |
| 5,410,297 | 4/1995 | Joseph et al. | 340/573 |
| 5,519,380 | 5/1996 | Edwards | 340/572 |
| 5,633,627 | 5/1997 | Newham | 340/573 |
| 5,654,694 | 8/1997 | Newham | 340/573 |
| 5,751,214 | 5/1998 | Cowley et al. | 340/573.4 |
| 5,780,798 | 7/1998 | Hall-Jackson | 340/573.4 |
| 5,796,059 | 8/1998 | Boon | 200/85 R |
| 5,808,552 | 9/1998 | Wiley et al. | 340/573.4 |
| 5,844,488 | 12/1998 | Musick | 340/573.4 |

*Primary Examiner*—Daniel J. Wu
*Assistant Examiner*—Tai T. Nguyen
*Attorney, Agent, or Firm*—Head, Johnson & Kachigian

[57] ABSTRACT

A monitoring system for a patient in a bed having a room number that provides a signal to a nurses station when the patient exits the bed including a sensor pad positioned on the bed responsive to the weight of a patient, a control unit adjacent the bed to which the sensor pad is connected, a display unit positioned adjacent the nurses station having a room number visual display and an audio signal generator and a radio signal transmitter in the control unit that transmits a radio signal upon actuation of the sensor pad and a radio receiver in the display unit that responds to sound an audio alarm and to visually display the patients room number.

6 Claims, 2 Drawing Sheets

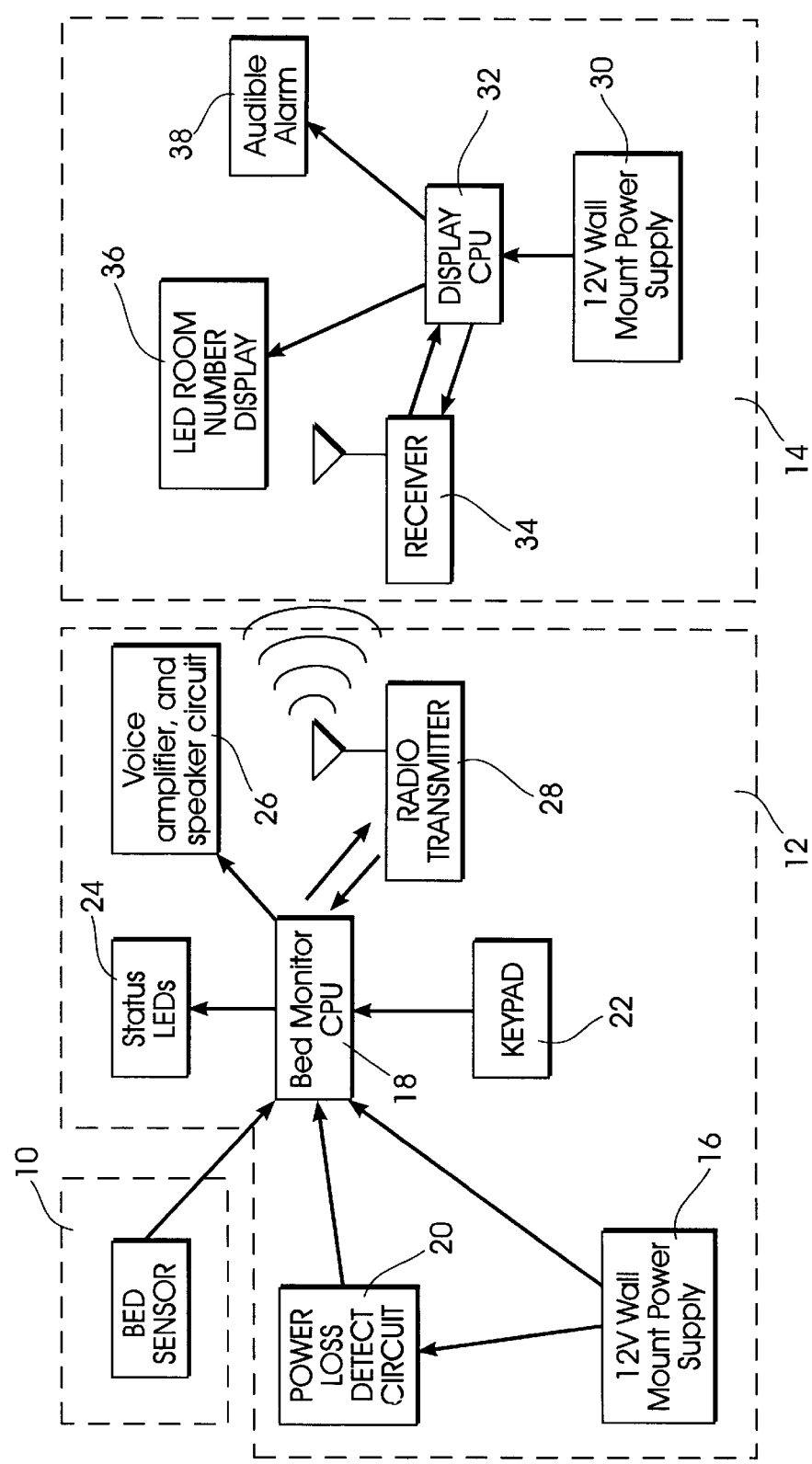

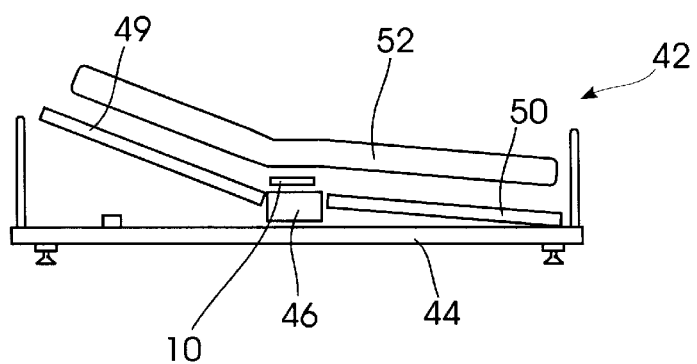
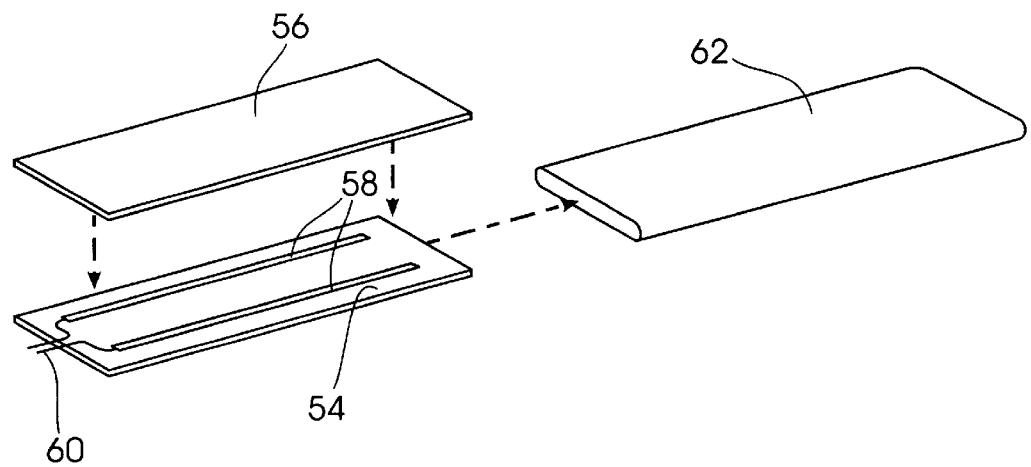

SYSTEM FOR MONITORING A BED PATIENT

REFERENCE TO PENDING APPLICATIONS

This application is not related to any pending United States or international patent application.

REFERENCE TO MICROFICHE APPENDIX

This application is not referenced in any Microfiche Appendix.

BACKGROUND OF THE INVENTION

A serious problem encountered by operators of hospitals, nursing homes, retirement centers and other facilities that take care of bed patients is that of patients leaving their beds and subsequently tripping or falling. Patients that are heavily medicated or sedated are particularly susceptible to falls. For these reasons much consideration has been given to systems for monitoring patients and providing a warning that a patient is in the process or has exited his or her bed.

For detailed background information relating to systems, methods and devices for monitoring bed patients, reference should be had to the following U.S. Patents:

| U.S. PAT. NO. | INVENTOR | TITLE |
| --- | --- | --- |
| 4,179,692 | Vance | Apparatus to Indicate When a Patient has Evacuated a Bed or Demonstrates a Restless Condition |
| 4,295,133 | Vance | Apparatus to Indicate When a Patient has Evacuated a Bed or Demonstrates a Restless Condition |
| 4,484,043 | Musick et al | Switch Apparatus Responsive to Pressure or Distortion |
| 4,565,910 | Musick et al | Switch Apparatus Responsive to Distortion |
| 4,700,180 | Vance | Apparatus to Indicate When a Patient has Evacuated a Bed |
| 4,907,845 | Wood | Bed Patient Monitoring System |
| 5,184,112 | Gusakov | Bed Patient Position Monitor |
| 5,633,627 | Newham | Hard-Wired Monitoring System for Hospital Bed or Short Term Care Patients |
| 5,654,694 | Newham | Mobile Battery Powered Patient Bed and Chair Occupancy Monitoring System |

BRIEF SUMMARY OF THE INVENTION

A monitoring system for a patient in a bed provides a signal to a nurse station when the patient exits the bed. A sensor pad is positioned on the patients bed. In a preferred arrangement the sensor pad is positioned under the bed mattress. The location of the sensor pad is important and is preferably positioned in the area where the maximum weight of the patient is normally distributed and typically this is under the mattress in the area under the hips of the patient. The sensor pad provides an electrical signal when at least a substantial portion of the weight of the patient is removed. By proper placement of the sensor pad a signal can be given when a patient is in the process of exiting the bed that is, before the patient actually fully leaves the bed. For instance, when a patient moves to the edge of the bed the sensor pad if properly positioned, will provide a signal.

A control unit is positioned in the room occupied by the patient, that is adjacent to the patients bed. The sensor pad is connected to the control unit.

A keypad connected to the control unit is used to program the system with the patients room number.

A receiver/display unit is positioned at a nurses station. The display unit is also a receiver unit as will be explained. The display unit can be mounted on the ceiling of the nurses station or located at any prominent position where it can be in constant visual view of a nurse or nurses. Further, the display unit includes an audio signal generator.

A radio signal transmitter in the control unit responds to a switch signal from the sensor pad when a significant portion of the weight of the patient is removed from the sensor pad. In response to the signal from the sensor pad, an electromagnetic radio signal is transmitted from the control unit to the display unit. Upon receipt of the radio signal the display unit sounds an audible alarm and simultaneously displays the room number of the patient.

When an alarm is sounded and the patient's room number is displayed, a nurse can leave the nurse's station and immediately proceed to the room to assist the patient that has exited or is in the process of exiting a bed to substantially reduce the chance that the patient will fall.

In a preferred embodiment of the invention, the control unit includes an audio message generator. When the sensor pad provides a signal indicating that at least a substantial portion of the weight of the patient has been removed from the sensor pad an audio message is broadcast in the patients room instructing the patient to lie back down. This message can be repeated more than once. If the patient responds to the message and lies back down so that his or her weight is again applied to the sensor then the radio frequency transmission and audio messages cease at both the control unit and the display unit. At this point the system automatically resets itself to a monitoring position. If the sensor pad does not immediately, within a predetermined number of seconds, detect that the patient has resumed normal position in the bed then the radio signal continues to transmit and alarm at the display unit and at the control unit.

The use of a radio signal to couple the control unit to the display unit permits the control unit to be freely moved from one room to another without requiring wiring. Further, by the ability to program the room number to be displayed in correspondence with the control unit that initiates a signal that a patient has left his or her bed allows the units to be freely moved from one room to another and quickly and easily reprogrammed to display the correct room number for the room being monitored. Further the use of radio frequency signals means that a large number of control units such as up to 100 as an example, can be monitored from a single display unit.

The system of this invention provides a bed monitoring arrangement that can be very expeditiously installed in a hospital or nursing home since it does not require any wiring between the control unit or control units and the display unit. The control unit can be plugged into a wall outlet and the sensor pad positioned under the mattress of the patient very expeditiously, therefore installing the system in each patients room takes only a few minutes and does not require tools of any kind. Similarly the display unit requires only to be plugged into a source of electrical power and positioned to be visually observable. The display unit can be constructed so that it is merely placed on top of a file cabinet so that the display unit can be installed in a few minutes and without tools. In some instances the display unit will be more preferably mounted on a wall or ceiling but other than connecting to a power source does not require any wiring. Therefore the entire system is very expeditiously installed and ready for operation compared to the more complex wiring systems required for previously known bed monitoring systems.

A more complete understanding of the invention will be obtained from the following description of the preferred embodiment, taken in conjunction with the attached drawings.

DESCRIPTION OF THE DRAWINGS

FIG. 1 is a block diagram of a components making up the system of this invention for monitoring a bed patient.

FIG. 2 is a diagrammatic elevational view of a typical hospital bed showing a central, generally stationary frame portion with a head portion and foot portion each of which is separately pivotal with respect to the center portion. This view shows a bed sensor positioned between the mattress and the bed central frame portion.

FIG. 3 is an exploded isometric view of components making up a bed sensor as used in this invention. FIG. 3 is illustrative of a typical bed sensor that may be employed to indicate the presence or absence of a patient from a selected portion of a hospital bed.

DETAILED DESCRIPTION OF A PREFERRED EMBODIMENT

The invention described herein provides a system for monitoring a bed patient and more specifically a system for monitoring a plurality of bed patients from a nurses station that is unique in the fact that the system can be very expeditiously installed in a facility having a number of beds to be monitored without requiring a skilled workman of any kind. In like manner, the system can be very readily moved from one location to another such as one wing of a hospital to another wing or from one floor to another. The system is readily expandable and is adaptable for monitoring one bed up to a hundred or more beds. The system does not require interaction with a nurse call system. While the system is particularly unique in its ease of installation it is also unique in its characteristic of being simple to operate and in its improved effectiveness in accurately indicating when a patient has left his or her bed and thereby be susceptible of falling.

FIG. 1 shows a block diagram of the elements making up the basic components of the system. The invention consists of three basic components, that is a bed sensor 10 a control unit 12 and a display unit 14. A sensor pad 10 and a control unit 12 are required for each patient to be monitored, however a large number patients such as up to one-hundred as an example, can be monitored with a single display unit 14.

Basically, bed sensor 10 is a device positioned on or in a hospital bed that functions to provide a signal indicating the presence or absence of a patient from a selected position on the bed. A typical bed sensor that can be employed in practicing this invention will be subsequently described in detail with respect to FIG. 3 and the typical use of a bed sensor 10 will be described with reference to a diagrammatic elevational view of a typical hospital bed as indicated in FIG. 2.

A control unit 12 is a relatively small enclosed box that can be made of wood, metal or plastic and that has an extension cord extending therefrom by which the control unit may be connected to a source of electrical power as represented by a wall mounted power supply 16. As an example, wall mounted power supply 16 may be a small 12-volt transformer having integral prongs plugged into a typical 110-volt A/C electrical outlet providing a 12-volt A/C output.

Within control unit 12 is a central processor 18 having a computer program therein provide the logic necessary to carry out the functions of the control unit. 10 Control unit 12 may be provided with a power backup so that the device functions even if voltage from power supply 16 should be a temporarily suspended such as if the device is inadvertently temporarily disconnected from a wall circuit outlet. The employment of a power loss detect circuit 20 as a part of control unit 12 is optional. Whereas the power for control unit 12 may be obtained, as previously indicated, by a plug-in type transformer it is also possible that the control unit 12 may be permanently wired to a source of electrical power in which case a transformer to step down the of the required voltage may be located directly within the housing that contains the other components of the control unit 12.

A part of the control unit 12 is a keypad 22 that may consist solely of numbered buttons 0–9 but that preferably also has an ON/OFF key, a HOLD key, an ENTER key and a VOLUME key. The keypad 22 is used in a way that will be explained in detail subsequently but it basically provides the function of keying into the CPU 18 the patients room number. As in a way that will be explained subsequently this room number information is conveyed to the display unit 14 so that the control unit 12 and display unit 14 function in a way to identify a signal emanating from control unit 12.

Control unit 12 may also include a status indicator such as status LED's 24 used to indicate that the unit is supplied with electrical energy necessary for its operation and its status may be further indicated such as whether the device is energized or de-energized.

Control unit 12 also includes a speaker circuit 26 that includes a speaker as a part thereof by which audio information is delivered to the patient being monitored by the control unit. As will be described subsequently, speaker circuit 26 is employed primarily to command the patient to lie back down but also provides audio feedback after operator performs each function on the keypad.

The other important component of control unit 12 is a radio frequency transmitter 28 that transmits electromagnetic energy (radio waves) that provides means of communicating between control unit 12 and display unit 14. Radio transmitter 28 may typically transmit a frequency modulated 900 MHz FM signal. This frequency is available for use without a license for applications of this type.

The major components of display unit 14 will now be explained. Display unit 14 requires electrical energy which could be a supplied by a battery but is more conveniently supplied from a 110-volt A/C wall outlet. The power supply indicated by numeral 30 may be a transformer having integral prongs that plug into a typical 110-volt A/C outlet or the power supply may be in the form of a transformer contained within a housing that houses the other components of display unit 14.

The components of display unit 14 are preferably contained in a small housing that can be made of metal, wood or plastic. The housing can be configured to sit on a flat horizontal surface or it can be configured to be attached to a wall or a ceiling.

It is important that display unit 14 be within easy vision of at least a majority of nurses that will be employed at the nurses station where display unit 14 is maintained. By "nurses station" is meant any location within a building where one or more persons is available to come to the aid of a patient in the room that contains control unit 12. The word "patient" is not limited to a person in a hospital or doctor's office or otherwise under care in a medical facility but is inclusive of elderly or infirm in a retirement center or any person who, because of his or her condition, whether permanently or temporarily is subject to loosing his or her balance or becoming disoriented if exiting a bed. In some instances the system can be used even where there is no significant danger of a person falling but wherein the personnel needs to know whether the person is in his or her bed or is out of it. Thus the terms "nurses station" and "patient" are both used herein in the broadest sense.

Display unit 14 that, as previously stated, also functions as a receiver, includes a central processor unit 32 in which a computer program is stored and is energized by power supply 30. Display unit 14 includes a radio frequency receiver 34 that is tuned to receive signals transmitted from the control unit transmitter 28 as previously described. As previously stated, typically transmitter 28 and receiver 34 are configured to transmit and receive on a readily available frequency that does not require the grant of an FCC license, such as 900 MHz FM. When a signal is received by receiver 34 an input is transmitted to central process unit 32 that generates two functions. First, the number of the room in which control unit 12 is located is visually displayed on room number display 36, such as by liquid crystal display numbers and/or letters so that nurses or attendants at the nurse call station will be immediately notified of the number of the room from which a radio signal has been broadcast indicating that a patient is preparing to or has left his or her bed. Simultaneously, CPU 32 energizes an audible alarm 38 to apprise nurses or attendants at the nurses station that a radio signal has been received so that they will know that a room number is being displayed on room number display 36. When actuated the room number and an audio alarm continue until a staff member has responded to the patient and has deactivated the control unit.

Typically, display unit 14 is designed to have a capacity to monitor as many as one-hundred or more rooms with an RF range of about 200 feet obstructed. Further, the CPU 32 is preferably designed with memory capabilities that allow it to store every action taking place for each control unit 12. In this way, if a patient exits from a bed and suffers a fall a record is available to determine if the control unit 12 was turned on and, if the unit was turned on, if it was on hold or if the alarm had sounded. Further, the program can also provide a record of the time required for a staff member to respond to an alarm in any room being monitored.

Each control unit 12 that is positioned in a room to monitor a patient has several features programmed into it. First, it has an audio voice feedback provided by speaker circuit 26 that assists a staff member when keying in the room number by means of keypad 22. This audio feedback provides an audio signal for each number keyed to avoid accidently putting in the wrong room number. After the room number is keyed in then the speaker circuit 26 repeats the room number. Further, as has been previously stated, speaker circuit 26 includes a voice recorded message that is activated if a patient tries to exit his or her bed. The message tells the patient to lie back down and that a staff member will be there to assist them. It repeats the message until a staff member arrives and places the patient back in bed. Or it will quit repeating the message if the patient lies back down on their own. When the patient lies back down in the bed the control unit recognizes, through the closed signal from bed sensor 10 that the patient is back in bed. At this moment, control unit 12 unit will automatically go back to its monitoring condition.

If a patient is off of sensor 10 with the alarm sounding and if the patient struggles with the attending staff member and will not lie back down. The HOLD key on keypad 22 that when depressed simulates sensor 10 being in a closed position thereby placing the system on HOLD. The HOLD key on keypad 22 also serves an additional function, that when depressed while the patient is still in bed, it allows a staff member to remove a patient from his or her bed without the alarm sounding. This feature allows a staff member to take a patient to therapy, to the bathroom, for X-Ray and so forth. When a patient is returned to his or her bed and placed onto sensor 10 the control unit will automatically reset itself to an on or monitoring condition.

Keypad 22 includes an automatic lock out system that prevents a patient or visitor from being able to turn the control unit off. The keypad is unlocked by depressing a star (*) key first so that only a staff member with this knowledge can turn the unit ON or OFF or any other keypad function. Further the system has an automatic reset so that a staff member does not have to turn the device on and off all the time when attending to a patient that is being monitored.

FIG. 2 is a diagrammatic representation of the way bed sensor 10 functions with a typical hospital bed. The hospital bed is indicated generally by the numeral 42 and includes a frame 44 that supports a stationary center frame 46. Extending from center frame 46 is a tiltable bed head portion 49 and extending in the other direction from stationary center frame 46 is a tiltable bed foot portion 50.

Positioned on top of support surfaces provided by stationary frame member 46, bed head portion 49 and bed foot portion 50 is a mattress 52 that is capable of flexing to bend when the bed head or foot portions 49, 50 are pivoted.

Bed sensor 10 is an elongated flat pressure sensing member that is positioned on stationary center frame 46. In this way, the major weight bearing portion of the body of a patient, that is, normally the hip portion, is centered over the bed sensor 10 whether the head portion 48 or foot portion 50 is tilted up or down.

An exploded view of a typical bed sensor is shown in FIG. 3, and includes a bottom plate 54 and an upper plate 56. Bottom plate 54 and upper plate 56 can each be made of stiff plastic material such as about ⅛ inch thick acrylic plastic or plexi-glass. Although, in some instances the top plate can be of ⅛ inch thickness and the bottom plate of ¼ inch thickness to provide a firmer base for the sensor pad. A pair of ribbon switches 58 are arranged parallel to each other on top of bottom plate 54 and thereby are sandwiched between bottom plate 54 and upper plate 56 when the plates are assembled. Ribbon switches that can be employed for making a bed sensor as illustrated in FIG. 3 are commercially available from Tapeswitch Corporation of Farmingdale, N.Y.

A conductor's 60 that extend from tape switches 58 out through the two plates 56 and 54, the conductor extending and connecting to the control unit 12 (as seen in FIG. 1) and within the control unit to central processor unit 18. The assembled bed sensor is encapsulated within a cover 62 in the form of a bag that is then preferably heat sealed to provide an impervious sealed environment within the bag for the sensor components. This sealed configuration permits the sensor to be cleaned with disinfectant and reused from patient to patient. Further, since the sensor does not contact the patient but is underneath the mattress on which the patient rests, the sensor is capable of reuse without the necessity of providing a new sensor for each new patient.

The sensor illustrated in FIG. 3 is by way of example only as other types of weight or pressure sensors are available.

The monitoring system preferably works in this way: (a) bed sensor 10 detects that the weight of the patient is removed and provides a vacating signal to CPU 18; (b) an audio message is generated by speaker circuit 26 commanding the patient to lie back down; (c) if the patient does not lie back down within a short prescribed time of a few seconds CPU 18 activates transmitter 28 to send a radio signal to display unit 14 to immediately actuate audible alarm 38 and room number display 36. In this way a signal is not sent to the display unit without giving the patient an opportunity to lie back down but at the same time the delay is sufficiently short that if the patient is actually in the process of exiting his or her bed, the display unit will be actuated simultaneously with or slightly before the patient has fully left his or her bed.

The system for monitoring a bed patient as described herein has advantages and improvements over other known systems particularly in the adaptability of the system to existing facilities in that the system can be installed to monitor a large number of rooms without hard wiring. The system can be installed very expeditiously without requiring skilled labor and particularly without requiring the need of an electrician or other technician. The system can just as easily and quickly be completely removed from a facility if no longer required. Further, the system is adaptable to adding additional rooms as required since only the placement of a control unit in a room and plugging a power cord from the control unit into an electrical outlet and the insertion of bed sensor 10 under the mattress of the bed is all that is required to add a new room to a monitoring system. Other features as have been described herein add significantly to improving the care of patients and particularly preventing falls or other accidents when patients evacuate their beds.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed:

1. A stand alone, wireless monitoring system for a patient in a bed having a room number that provides a signal to a remotely located nurses station when the patient exits the bed, comprising:

a sensor pad positioned on the bed responsive to the weight of a patient and providing a switch signal when at least a substantial portion of the weight of a patient is removed from the sensor pad;

a control unit adjacent the bed to which said sensor pad is connected;

a keypad connected as a part of said control unit by which the patients room number is programmed;

a display unit positioned adjacent a remotely located nurses station having a room number visual display and an audio signal generator; and a radio signal transmitter in said control unit responsive to a switch signal from said sensor pad that transmits an electromagnetic signal upon actuation of said sensor pad, said remotely located display unit having means to receive said radio signal and in response thereto to sound an audio alarm and to visually display said room number, said sensor pads control unit, keypad, display unit and radio signal transmitter being isolated from and independent of any other nurses call system.

2. A monitoring system according to claim 1 including:

an audio message generator in said control unit responsive to said sensor pad switch signal providing an audio message commanding the patient to lie back down when said sensor pad first provides a switch signal.

3. A monitoring system according to claim 2 including a time delay circuit in said control unit that delays for a preselected time said transmission of said radio signal following said sensor pad signal to allow time to first provide said audio message commanding the patient to lie back down.

4. A monitoring system according to claim 3 wherein said time delay is such that transmission of said radio signal takes place only if the patient does not respond to deactivate said sensor pad within a preselected time following an audio command to lie back down.

5. A monitoring system according to claim 1 including on said keypad a HOLD key to deactivate said sensor pad switch signal to allow a patient to be absent from the bed without the transmission of a radio signal to said display unit.

6. A monitoring system according to claim 1 wherein said sensor pad is in the form of an elongated, relatively thin flexible strip having a pair of conductors extending therefrom and having means to provide a first signal when the weight of a patient is impressed on said strip and a second signal when the weight of a patient is removed from said strip.

* * * * *